US00PP30025P3

(12) United States Plant Patent
Biancheri

(10) Patent No.: US PP30,025 P3
(45) Date of Patent: Dec. 25, 2018

(54) ***RANUNCULUS ASIATICUS* 'ABUMBREON'**

(50) Latin Name: *Ranunculus asiaticus*
Varietal Denomination: ABUMBREON

(71) Applicant: Alberto Biancheri, Camporosso Mare (IT)

(72) Inventor: Alberto Biancheri, Camporosso Mare (IT)

(73) Assignee: Impresa Individuale Biancheri Alberto (IT)

( * ) Notice: Subject to any disclaimer, the term of this patent is extended or adjusted under 35 U.S.C. 154(b) by 0 days.

(21) Appl. No.: 15/731,509

(22) Filed: Jun. 20, 2017

(65) Prior Publication Data

US 2018/0042157 P1 Feb. 8, 2018

(30) Foreign Application Priority Data

Aug. 5, 2016 (QZ) ..... PBR 2016/1916

(51) Int. Cl.
*A01H 5/02* (2018.01)

(52) U.S. Cl.
USPC ..... Plt./263.1
CPC ..... *A01H 5/02* (2013.01)

(58) Field of Classification Search
None
See application file for complete search history.

*Primary Examiner* — Anne Marie Grunberg
(74) *Attorney, Agent, or Firm* — Cassandra Bright

(57) ABSTRACT

A new and distinct *Ranunculus* cultivar named 'ABUMBREON' is disclosed, characterized by an intense black color to the flowers. The flower size is medium, double flowers are produced throughout the flowering season. The new variety is a *Ranunculus*, normally produced as a cut flower and potentially useful as an ornamental plant.

2 Drawing Sheets

Figure 1:
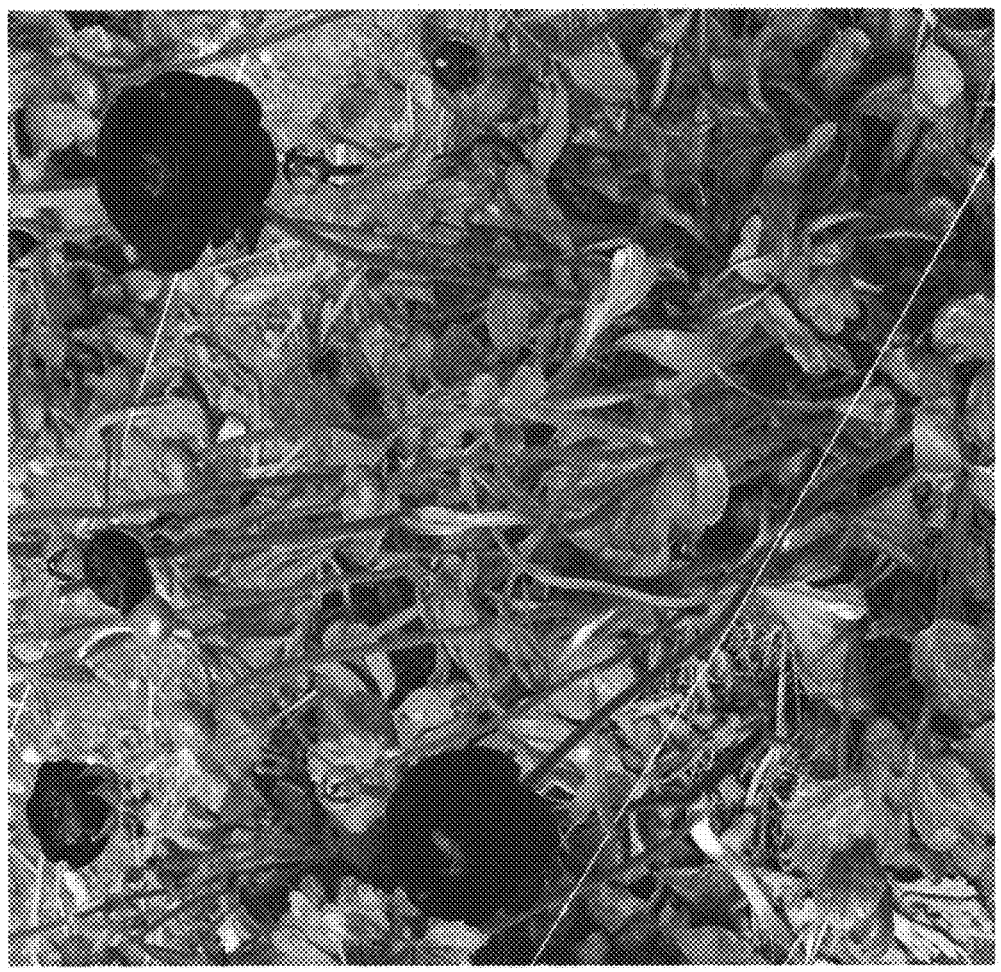
Figure 3:
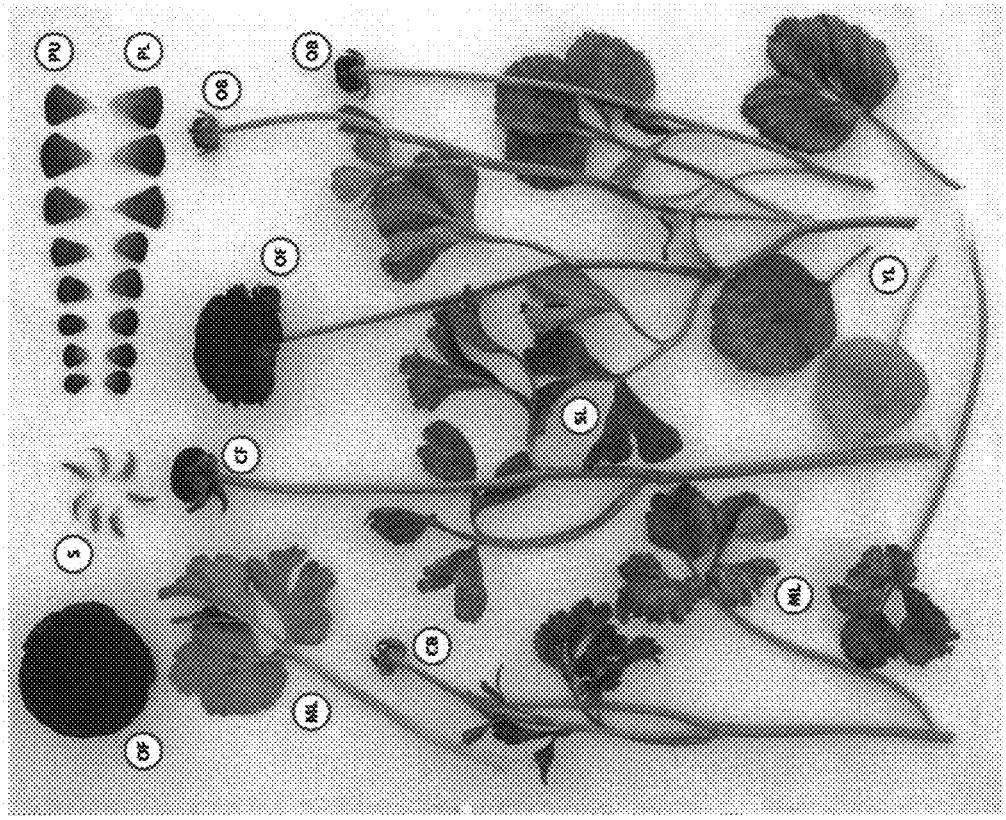

Latin name of the genus and species: *Ranunculus asiaticus*.

Variety denomination: 'ABUMBREON'.

BACKGROUND OF THE INVENTION

The new *Ranunculus* cultivar is a product of a planned breeding program conducted by the inventor, Alberto Biancheri in Camporosso Mare, Italy. The cross resulting in this new variety was made during 2007.

The seed parent is the, unpatented, proprietary variety referred to as *Ranunculus* 'N 240-04'. The pollen parent is the unpatented, proprietary variety referred to as *Ranunculus* 'N28-2000/2'. The new variety was discovered in 2012 by the inventor in a group of seedlings resulting from the 2007 crossing, in a research greenhouse in Camporosso Mare, Italy.

Asexual reproduction of the new cultivar was first performed by vegetative division of buds sprouting from the rhizome of the selected plant. Subsequent propagation has been performed by tissue culture. First propagation took place at a research greenhouse in Camporosso Mare, Italy in 2012 and has shown that the unique features of this cultivar are stable and reproduced true to type in multiple successive generations.

SUMMARY OF THE INVENTION

The cultivar 'ABUMBREON' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ABUMBREON' These characteristics in combination distinguish 'ABUMBREON' as a new and distinct *Ranunculus* cultivar:

1. Intense black coloration to the flowers.
2. Medium flower size.
3. Double flower throughout flowering season.
4. Highly productive plant.

PARENT COMPARISON

Plants of the new cultivar 'ABUMBREON' are similar to plants of the seed parent, in most horticultural characteristics, however, plants of the new cultivar 'ABUMBREON' differ in the following;

1. The new variety produces more petals, having a double flower compared to the semi-double flower of the seed parent.
2. Flower size of the new variety is larger, having an average diameter of 8.5 to 9.5 cm compared to an average diameter of 6.5 to 8.5 cm as found in the seed parent.
3. The new variety produces more flowering stems than the seed parent.

Plants of the new cultivar 'ABUMBREON' are similar to plants of the pollen parent, in most horticultural characteristics, however, plants of the new cultivar 'ABUMBREON' differ in the following;

1. Petal quantity of the new variety is higher, having a double flower compared to the semi-double flower of the pollen parent.
2. Flower size of the new variety is larger, having an average diameter of 8.5 to 9.5 cm compared to an average diameter of 6 to 8 cm found in the pollen parent.

3. The new variety produces more flowering stems than the pollen parent.

COMMERCIAL COMPARISON

Plants of the new cultivar 'ABUMBREON' are comparable to the unpatented commercial variety *Ranunculus* 'ABIOSHEKA'. The two *Ranunculus* varieties are similar in most horticultural characteristics; however, the new variety 'ABUMBREON' differs in the following:

1. Flower color of the new variety is nearly black, flower color of this comparator is medium to dark purple.
2. Floral size of the new variety is smaller.
3. Foliage arrangement of the new variety is different than this comparator.

BRIEF DESCRIPTION OF THE PHOTOGRAPHS

The accompanying photograph in FIG. 1 illustrates in full color flowering plants of the new variety at approximately five months old, grown in a greenhouse.

FIG. 2 illustrates a close up of plant parts.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ edition, except where general terms of ordinary dictionary significance are used. The following observations and measurements describe 'ABUMBREON' plants grown in a greenhouse Camporosso Mare, Italy. The plant described has been cultivated under glass, planted in the months of September and described in the month of February. One must always refer to these conditions of season and culture, when considering the present description. By reason of different climate or culture conditions, differences may arise between certain characteristics of the plant and the corresponding characteristics of the description. It should be considered as normal and do not modify the essence of the present invention because it will possible to identify the plant by means of the totality of the characteristics given in the description. The rhizome has been planted on raised benches in a peat and pumice substrate mixture. The growing temperature ranged from 12° C. to 25° C. during the day and from 2° C. to 8° C. during the night. General light conditions are bright, normal sunlight. Measurements and numerical values represent averages of typical plant types.

Botanical classification: *Ranunculus asiaticus* 'ABUMBREON'.

PROPAGATION

Time to rooting: 15 days at approximately 10-12° C.

Time to produce a rooted plantlet: 20 days.

Root description: Secondary roots grow from the rhizome and are fasciculate type.

PLANT

Growth habit: Herbaceous perennial, robust plant, semi-erect vegetation.

Height to top flower: 50 to 60 cm.

Plant spread: 35 to 40 cm.

Growth rate: Medium.

Branching characteristics: Main floral stems grow from a basal rosette with 1 or 2 lateral branches, each one of which has a flower.

Length of lateral branches: 45 to 55 cm.

Diameter of lateral branches: 0.8 to 1.0 cm.

Texture of lateral branches: Slightly tomentose.

Internode length: Internodes are extremely close together, forming a basal rosette.

Strength of lateral branches: Medium.

Color of Lateral branches: Yellow Green (RHS 144A).

Aspect to angle of branches: 20° to 25°.

Number of leaves per lateral branch: Usually 2.

Foliage: The leaves, usually numerous, have a marked heterophyllia, in relation to the degree of their development and their position on the plant (base of the plant; floral stem).

Leaf at the base of the plant:

*Arrangement.*—Simple (young leaf, YL); Biternate (mature leaf, ML).

*Average length.*—27 to 32 cm.

*Average width.*—10 to 20 cm.

*Overall shape of blade.*—Obovate (young leaf); Palmatipartite (mature leaf).

*Dissected leaves, describe lobes, quantity of dissection.*—Young leaves are generally not lobed; mature leaves are generally divided in 3 parts, each one of which is further divided.

*Apex.*—Rounded.

*Base.*—Rounded.

*Attachment.*—Base of the plant.

*Margin.*—Crenate.

*Texture of top surface.*—Slightly tomentose, verrucose, spotted.

*Texture of bottom surface.*—Slightly tomentose, Rugose.

*Appearance of top surface.*—Matte.

*Appearance bottom surface.*—Glossy.

*Leaf internode length.*—The internodes are extremely close together, forming a basal rosette.

*Color.*—Young foliage upper side: Green (RHS 137A); Yellow Green (RHS 144A) spotted. Young foliage under side: Yellow Green (RHS 146B). Mature foliage upper side: Green (RHS 137A); Yellow Green (RHS 144A) spots. Mature foliage under side: Yellow Green (RHS 146B).

*Venation.*—Type: Palmate; plunging in to the limb at the upper surface; very raised on the limb at the lower surface. Venation color upper side: Yellow Green (RHS 144A). Venation color under side: Yellow Green (RHS 144A).

*Petiole.*—Petiole: Long, tubular, rigid. Length: 17 to 23 cm. Diameter: 0.5 to 0.6 cm. Pubescence: Slightly tomentose. Color: Yellow Green (RHS 144A).

Leaf inserted at the nodes of the floral stems (SL):

*Arrangement.*—Bitemate.

*Average length.*—15 to 25 cm.

*Average width.*—12 to 15 cm.

*Overall shape of blade.*—Palmatipartite.

*Dissected leaves, describe lobes, quantity of dissection.*—Generally divided in 3 parts, each one of which further is divided in many deeply incised lobes.

*Apex.*—Rounded.

*Base*.—Acute.
*Attachment*.—Floral stems.
*Margin*.—Dentate.
*Texture of top surface*.—Slightly tomentose.
*Texture of bottom surface*.—Slightly tomentose.
*Appearance of top surface*.—Glossy.
*Appearance bottom surface*.—Glossy.
*Leaf internode length*.—8 to 10 cm.
*Color*.—Foliage upper side: Green (RHS 137B). Foliage under side: Green (RHS 138A).
*Venation*.—Type: Dichotomous, plunging in to the limb at the upper surface and raised on the limb at the lower surface. Venation color upper side: Yellow Green (RHS 144A). Venation color under side: Yellow Green (RHS 144A).
*Petiole*.—Petiole: Long, slightly flat, rigid. Length: 4 to 14 cm. Diameter: 0.4 to 0.6 cm. Pubescence: Slightly tomentose.
*Color*.—Yellow Green (RHS 144A).

FLOWER

Bloom period: Winter to Spring.
Vase life (cut flower): 10 to 15 days.
Persistent or self-cleaning: Self-Cleaning.
Bud:
*Closed bud* (*CB*).—Shape: Flattened globular with a sharp point. Length: 0.9 to 2.2 cm. Diameter: 1.3 to 2.2 cm. Color: Green (RHS 137B) and Red Purple (RHS 59A) mixed together.
*Slightly open bud* (*OB*).—Shape: Flattened globular. Length: 1.9 to 2.2 cm. Diameter: 2.3 to 2.6 cm. Color: Black (RHS 202) fading to Purple (RHS N77A) from the margin to the base.
Flower size (OF):
*Diameter*.—8.5 to 9.5 cm.
*Height*.—2.8 to 3.6 cm.
Corolla (OF): Round, regular, in the form of a flat section.
Petals:
*Arrangement*.—Imbricated, disposed on the receptacle in very tight verticils. The size of the petals is quite variable, according to the position in the corolla, decreasing from the exterior toward the center. The average size of fully developed petal is as follows.
*Lobe length*.—4.5 to 5.0 cm.
*Lobe width*.—3.5 to 4.5 cm.
*Quantity*.—Double flower, petals are very numerous an average range can be 200.
*Texture*.—Silky, thin, resistant.
*Lobe apex*.—Rounded.
*Lobe shape*.—Obovate.
*Margin*.—Crenulate.
*Aspect*.—Fan shape, concave, slightly reflexed when flower is fully opened.
Color when opening (CF):
*Upper surface*.—Black (RHS 202) fading to Purple (RHS N77A) from the margin towards the base.
*Lower surface*.—Black (RHS 202) fading to Purple (RHS N77A) from the margin towards the base.
Color Fully opened (OF):
*Upper surface* (*PU*).—Red Purple (RHS 59A) fading to Purple (RHS N79C) from the margin towards the base.
*Lower surface* (*PL*).—Red Purple (RHS 59A) fading to Purple (RHS N79C) from the margin towards the base.
Calyx to sepals (S):
*Quantity per flower*.—4 to 6.
*Shape*.—Concave, slightly incurved.
*Length*.—2.0 to 3.0 cm.
*Width*.—1.0 to 1.4 cm.
*Apex*.—Acute.
*Base*.—Flat to Slightly rounded.
*Margin*.—Entire
*Texture*.—Lower surface is tomentose; Upper surface is glabrous.
*Color upper surface*.—Yellow Green (RHS 146B).
*Color lower surface*.—Green (RHS 137B); Red Purple (RHS 59A) along venation.
Peduncle: None.
Pedicel:
*Length*.—45 to 55 cm.
*Diameter*.—0.8 to 1.1 cm.
*Color*.—Strong Yellow Green (RHS 144A).
*Orientation*.—Upright, straight, rigid.
*Pubescence*.—Slightly tomentose.
Fragrance: None.

REPRODUCTIVE ORGANS

Androecium:
*Stamens*.—Almost completely transformed as petals.
Gynoecium: The pistils are numerous, short, fused together at the center of the corolla in a Purple (RHS N79A) large, flattened, dome-shaped apocarpous gynoecium with a Yellow Green (RHS 144A) central rift.

OTHER CHARACTERISTICS

Seeds and fruits: Seeds and fruit production not observed.
Disease to pest resistance: Neither resistance nor susceptibility to normal diseases and pests of *Ranunculus* has been observed.
Temperature tolerance: Upper and lower temperature tolerance not observed, plants have been grown in a climate controlled greenhouse. *Ranunculus asiaticus* typically tolerates temperatures within USDA Zones 7 to 11.

What is claimed is:

1. A new and distinct cultivar of *Ranunculus* plant named 'ABUMBREON' as herein illustrated and described.

* * * * *